United States Patent [19]

Yoshida

[11] Patent Number: Plant 5,597

[45] Date of Patent: Dec. 10, 1985

[54] AFRICAN VIOLET (RHONDA)

[76] Inventor: Eiichi Yoshida, P.O. Box 4836, Hayward, Calif. 94540

[21] Appl. No.: 579,179

[22] Filed: Feb. 10, 1984

[51] Int. Cl.[4] ..... A01H 5/00

[52] U.S. Cl. ..... Plt./69

[58] Field of Search ..... Plt./69

*Primary Examiner*—Robert E. Bagwill

[57] ABSTRACT

A new variety of African violet plant for potted plant culture particularly distinguished by its year around blooming capability, its profuse production of pink ruffled-edged flowers and its compact, girl-leaf foliage of solid green color. An ideal plant for small potted plant production.

1 Drawing Figure

BACKGROUND OF THE NEW PLANT

To obtain this new variety of African violet plant, the inventor cross-pollenated the seed parent "Melodie" Mitzi Saintpaulia and the pollen parent Breeding Stock #XX-79 Saintpaulia. The seed pods of the pollenated plants were used as the generic basis for initiating further experimental series. Approximately 25 seedlings were selected by very rigid standards for further propagation. Propagation of these plants and refinement out of limited selected plants continued and tests were conducted for the development of permanent characteristics of disease resistance, early blooming and vigorous growth.

The descendants of the original plants were completely the same in appearance as the parent plant.

DESCRIPTION OF THE PLANT

Sheet one is a full color photographic view of the plant in bloom, the colors shown being as nearly true as it is reasonably possible to obtain by conventional photographic procedures.

The following is a detailed description of my new African violet plant with the color designation being accorded to The R.H.S. Colour Chart published by The Royal Horticultural Society of London, England, with collaboration by the British Colour Council.

THE PLANT

Origin: Seedling, #H-311/12.

Parentage:

*Seed parent.*—"Melodie" Mitzi.

*Pollen parent.*—Breeding Stock #XX-79.

Classification:

*Botanic.*—Saintpaulia Ionanthe.

*Commercial.*—African Violet.

Form: Rosette arrangement.

Height: 8.5 to 11.7 cm. tall.

Growth: New growth is vigorous and has a tendency to grow slightly upwards. As leaves get older they grow more horizontally and eventually grow somewhat downward.

Size: Small; overall plant diameter is from 16.2 to 17.5 cm.

Mutation prone: Very little for flowers or foliage.

Foliage: Brittle, girl-type.

*Shape.*—Oval with crenate margins.

*Length.*—Approximately 7 cm. for a mature leaf.

*Width.*—Approximately 7 cm. for a mature leaf.

*Color.*—Upperside: Medium green, light green at the petiole. Underside: Light green.

*Texture.*—Upperside: Puberrulent. Underside; Puberulent.

*Ribs and veins.*—Pinnate, slightly sunken on leaf surface, pronounced on underside of leaf.

*Petiole.*—Round with a small, U-shaped groove on top along its length. Red pigment present, darker on top. Pubescent on top, puberulent on its underside. Length varies with age of leaf and plant.

THE FLOWER

Blooming habit: Continuous and abundant under optimum growing conditions. Very early first first bloom.

Number: Four to twelve per peduncle.

Size of flower: Each flower is from 4.1 to 4.8 cm. in diameter.

Color: Red-purple group, 62-B, from The R.H.S. Colour Chart.

Type: Single

Petals: Five per individual flower with ruffled margins.

Texture: Smooth and flexible.

Appearance: Sparkly on upper surface. Underside is shiny with small bumps and is puberulent.

Peduncles: Short, strong, red pigmented, puberulent.

Inflorescence: Cyme, upright, above foliage.

Calyx: Quinquepartite, green with a small bit of red pigment, puberulent.

Persistence: Flowers do not drop. Old flowers dry up on the stalk.

Fragrance: None.

REPRODUCTIVE ORGANS

Stamens: Usually two per flower and joined at top of anthers.

*Anthers.*—Visible, bright yellow, fade slightly as they get older; one on each filament.

*Filaments.*—Approximately 0.4 cm. long.

*Pollen.*—Light yellow, ripens before stigma.

Pistils: Normally one per flower.

*Stigma.*—Usually visible and accessible. When receptive, it becomes swollen and usually exudes a small drop of clear fluid.

*Style.*—Approximately 0.7 cm. long.

*Ovary.*—Superior.

OTHER CHARACTERISTICS

This variety of African violet plant is very suited for potted plant culture and its year around blooming and very early blooming capabilities give the plant a commercially attractive value.

I claim:

1. An African Violet plant substantially as shown and described.

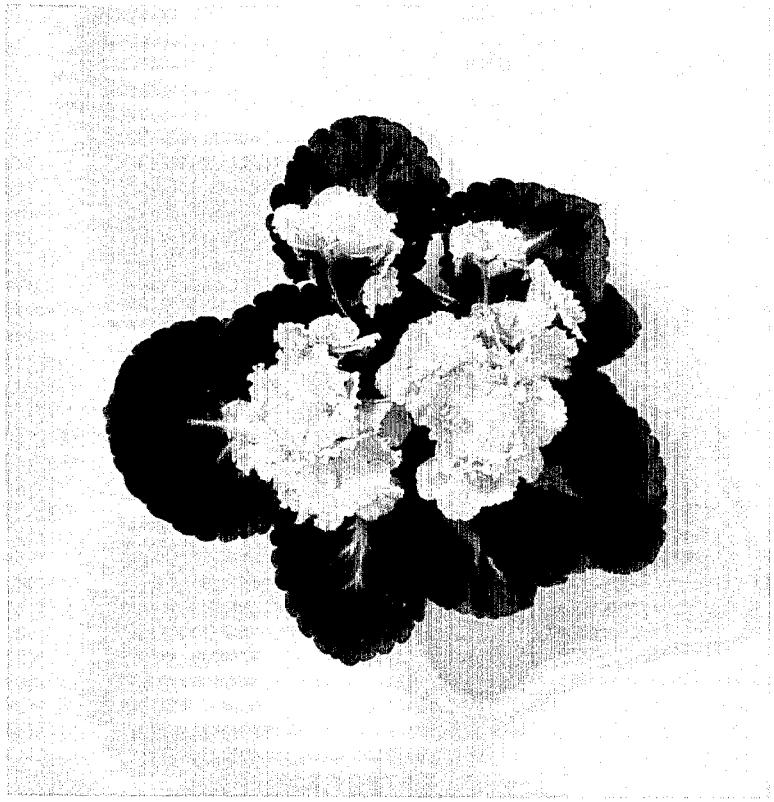

* * * * *